(12) United States Patent
Hayashi et al.

(10) Patent No.: US 10,980,414 B2
(45) Date of Patent: Apr. 20, 2021

(54) OPHTHALMOLOGIC APPARATUS

(71) Applicant: TOPCON CORPORATION, Tokyo (JP)

(72) Inventors: Takefumi Hayashi, Wako (JP); Yoko Tatara, Kita-ku (JP); Shunichi Morishima, Kawagoe (JP)

(73) Assignee: TOPCON CORPORATION, Tokyo (JP)

(*) Notice: Subject to any disclaimer, the term of this patent is extended or adjusted under 35 U.S.C. 154(b) by 178 days.

(21) Appl. No.: 16/289,675

(22) Filed: Mar. 1, 2019

(65) Prior Publication Data
US 2019/0282083 A1    Sep. 19, 2019

(30) Foreign Application Priority Data

Mar. 16, 2018  (JP) .............................. JP2018-049542

(51) Int. Cl.
| | |
|---|---|
| *A61B 3/10* | (2006.01) |
| *A61B 3/103* | (2006.01) |
| *A61B 3/107* | (2006.01) |
| *A61B 3/12* | (2006.01) |
| *A61B 3/00* | (2006.01) |
| *A61B 3/14* | (2006.01) |
| *A61B 3/16* | (2006.01) |

(52) U.S. Cl.
CPC ............ *A61B 3/102* (2013.01); *A61B 3/103* (2013.01); *A61B 3/1005* (2013.01); *A61B 3/107* (2013.01); *A61B 3/1035* (2013.01); *A61B 3/12* (2013.01); *A61B 3/0025* (2013.01); *A61B 3/14* (2013.01); *A61B 3/16* (2013.01)

(58) Field of Classification Search
CPC ........... A61B 3/14; A61B 3/0025; A61B 3/12; A61B 3/102

USPC ....................................................... 351/206
See application file for complete search history.

(56) References Cited

U.S. PATENT DOCUMENTS

| | | | |
|---|---|---|---|
| 2009/0128778 A1* | 5/2009 | Honda .................... | A61B 3/107 351/245 |
| 2017/0245756 A1 | 8/2017 | Hayashi et al. | |
| 2019/0008378 A1* | 1/2019 | Hayashi ............... | A61B 3/1005 |

FOREIGN PATENT DOCUMENTS

| | | |
|---|---|---|
| EP | 3 210 526 A1 | 8/2017 |
| JP | 2017-136215 A | 8/2017 |
| WO | 2017/135015 A1 | 8/2017 |

OTHER PUBLICATIONS

European Extended Search Report dated Aug. 21, 2019 in European Application No. 19160237.4-1124.

* cited by examiner

*Primary Examiner* — Mohammed A Hasan
(74) *Attorney, Agent, or Firm* — Xsensus LLP

(57) ABSTRACT

An ophthalmologic apparatus includes an objective lens, a refractive power measurement optical system, an inspection optical system, and an optical path separating unit. The refractive power measurement optical system is configured to project light in a first wavelength range onto a subject's eye via the objective lens and to detect returning light from the subject's eye. The inspection optical system is configured to project light in a second wavelength range onto the subject's eye via the objective lens. The optical path separating unit that is arranged in an optical path of the refractive power measurement optical system and is configured to separate an optical path of the inspection optical system from the optical path of the refractive power measurement optical system by performing wavelength separation based on changeable wavelength separation characteristics.

11 Claims, 9 Drawing Sheets

OPHTHALMOLOGIC APPARATUS

CROSS-REFERENCE TO RELATED APPLICATION

This application is based upon and claims the benefit of priority from Japanese Patent Application No. 2018-049542, filed Mar. 16, 2018; the entire contents of which are incorporated herein by reference.

FIELD

Embodiments according to the present invention relates to an ophthalmologic apparatus.

BACKGROUND

Ophthalmologic apparatuses capable of performing a plurality of inspections and measurements for a subject's eye are known. The inspections and the measurements for the subject's eye include a subjective inspection and an objective measurement. The subjective inspection is to acquire the result based on the responses from the subject. The objective measurement is to acquire information on the subject's eye mainly by the use of a physical method without referring to the responses from the subject.

For example, Japanese Unexamined Patent Application Publication No. 2017-136215 discloses an ophthalmologic apparatus that is capable of performing a subjective inspection and a refractive power measurement for the subject's eye and performing imaging and measuring by using optical coherence tomography.

SUMMARY

The first aspect of an ophthalmologic apparatus according to some embodiments includes an objective lens; a refractive power measurement optical system configured to project light in a first wavelength range onto a subject's eye via the objective lens and to detect returning light from the subject's eye; an inspection optical system configured to project light in a second wavelength range onto the subject's eye via the objective lens; and an optical path separating unit that is arranged in an optical path of the refractive power measurement optical system and is configured to separate an optical path of the inspection optical system from the optical path of the refractive power measurement optical system by performing wavelength separation based on changeable wavelength separation characteristics.

In the second aspect of the ophthalmologic apparatus according to some embodiments, in the first aspect, the wavelength separation characteristics are changed so as to perform wavelength separation for the light in the first wavelength range and the light in the second wavelength range according to a type of inspection.

In the third aspect of the ophthalmologic apparatus according to some embodiments, in the second aspect, the refractive power measurement optical system is arranged in an optical path of light reflected by the optical path separating unit, the inspection optical system is arranged in an optical path of light transmitted through the optical path separating unit, and the wavelength separation characteristics are changed so that the light in the first wavelength range is reflected by the optical path separating unit and the light in the second wavelength range is transmitted through the optical path separating unit when a measurement is performed with the refractive power measurement optical system and are changed so that the light in the first wavelength range is transmitted through the optical path separating unit and the light in the second wavelength range is transmitted through the optical path separating unit when an inspection is performed with the inspection optical system.

In the fourth aspect of the ophthalmologic apparatus according to some embodiments, in the second aspect, the refractive power measurement optical system is arranged in an optical path of light transmitted through the optical path separating unit, the inspection optical system is arranged in an optical path of light reflected by the optical path separating unit, and the wavelength separation characteristics are changed so that the light in the first wavelength range is transmitted through the optical path separating unit and the light in the second wavelength range is reflected by the optical path separating unit when a measurement is performed with the refractive power measurement optical system and are changed so that the light in the first wavelength range is reflected by the optical path separating unit and the light in the second wavelength range is reflected by the optical path separating unit when an inspection is performed with the inspection optical system.

In the fifth aspect of the ophthalmologic apparatus according to some embodiments, in any one of the first aspect to the fourth aspect, the optical path separating unit includes: two or more wavelength separation elements that have different wavelength separation characteristics each other; and a movement mechanism configured to selectively arrange the two or more wavelength separation elements in the optical path of the refractive power measurement optical system.

In the sixth aspect of the ophthalmologic apparatus according to some embodiments, in any one of the first aspect to the fifth aspect, the inspection optical system includes: a fixation optical system configured to project fixation light onto the subject's eye; and an optical path coupling member that combines an optical path of the fixation optical system with an optical path of the light in the second wavelength range, and the wavelength separation characteristics are changed so as to guide the fixation light to the objective lens when a measurement is performed with the refractive power measurement optical system and when an inspection is performed with the inspection optical system.

In the seventh aspect of the ophthalmologic apparatus according to some embodiments, in any one of the first aspect to the sixth aspect, the inspection optical system includes an interference optical system configured to split the light in the second wavelength range from a light source into reference light and measurement light, to project the measurement light onto the subject's eye, and to detect interference light between returning light of the measurement light from the subject's eye and the reference light.

In the eighth aspect of the ophthalmologic apparatus according to some embodiments, in any one of the first aspect to the sixth aspect, the inspection optical system includes a subjective inspection optical system configured to project visual target light in the second wavelength range onto the subject's eye, and the wavelength separation characteristics have characteristics of guiding the visual target light to the objective lens when the inspection is performed with the subjective optical system.

In the ninth aspect of the ophthalmologic apparatus according to some embodiments, in any one of the first aspect to the sixth aspect, at least a part of the inspection optical system is configured to be capable of replacing with an optical system included in any of two or more measurement units which are selectively attachable.

In the tenth aspect of the ophthalmologic apparatus according to some embodiments, in the ninth aspect, the two or more measurement units include: a first measurement unit including an interference optical system configured to split the light in the second wavelength range from a light source into reference light and measurement light, to project the measurement light onto the subject's eye, and to detect interference light between returning light of the measurement light from the subject's eye and the reference light; and a second measurement unit including a subjective inspection optical system configured to visual target light in the second wavelength range onto the subject's eye.

DETAILED DESCRIPTION

Figure 1:
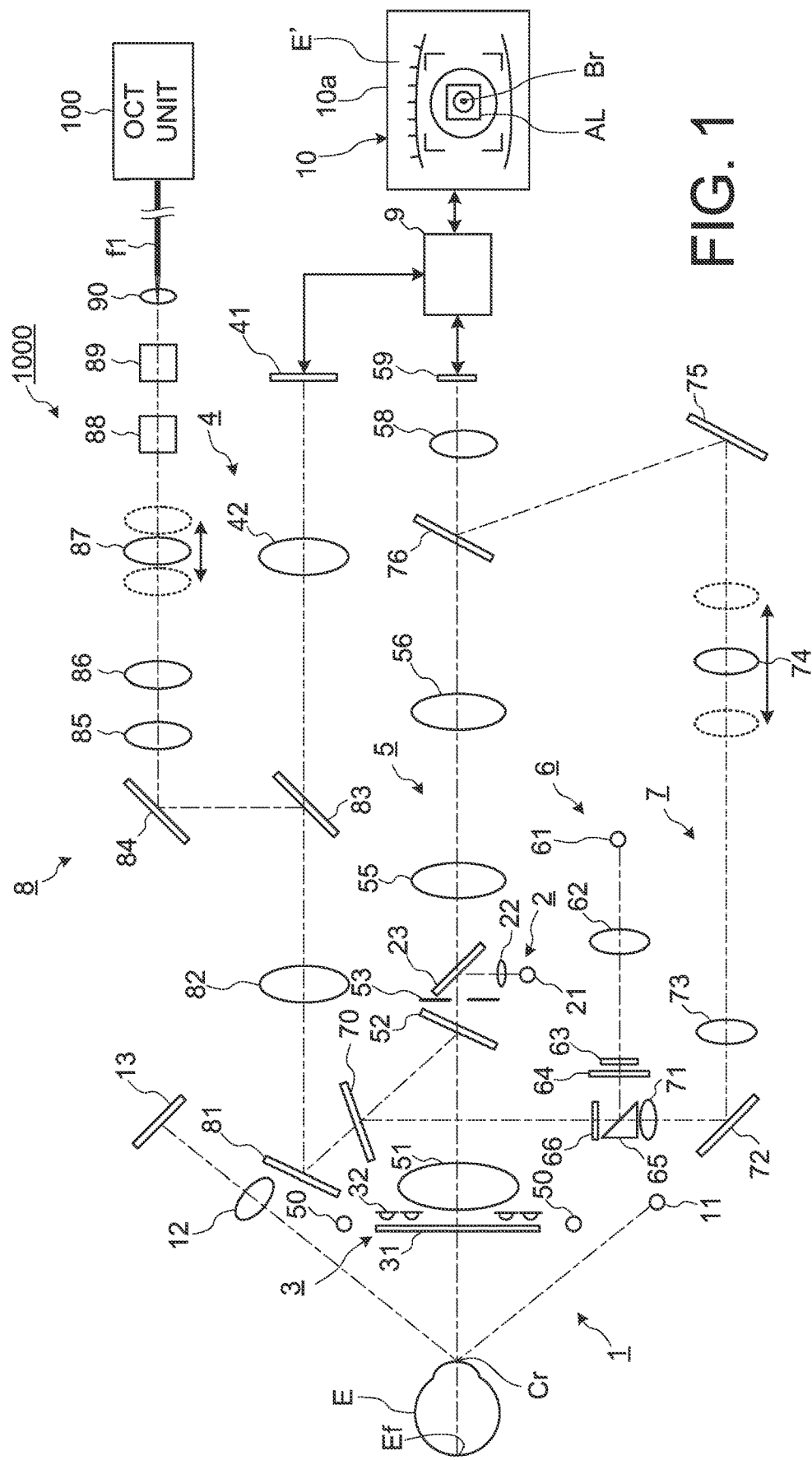
FIG. 1 is a schematic diagram illustrating an example of a configuration of an optical system of an ophthalmologic apparatus according to embodiments.

An ophthalmologic apparatus is provided with an observation optical system for observing an anterior segment or a fundus of a subject's eye, for example. By sharing the observation optical system with a plurality of optical systems each of which corresponds to the type of inspection (type of measurement), the ophthalmologic apparatus can be downsized. The plurality of the optical systems is wavelength-separated by a dichroic mirror, for example. For example, light in different wavelength ranges are used in each of the optical systems.

In an inspection or a measurement with the ophthalmologic apparatus, light in the wavelength range of the near infrared region is often used to reduce the burden on the subject. In this case, it is necessary to contrive the arrangement of the optical systems so that the wavelength ranges of the light used in each optical system do not overlap each other. It involves adding an optical member as necessary. Adding the optical member leads to an increase in size of the ophthalmologic apparatus.

According to some embodiments of the present invention, a new technique for performing a plurality of measurements and inspections with a simple configuration can be provided.

Referring now to the drawings, exemplary embodiments of an ophthalmologic apparatus according to the present invention are described below. Any of the contents of the documents cited in the present specification and arbitrary known techniques may be applied to the embodiments below.

The ophthalmologic apparatus according to the embodiments is capable of performing an objective measurement at least. The objective measurement is a method for measurement to acquire information on the subject's eye mainly by the use of a physical method without referring to the responses from the subject. The objective measurements include a measurement for acquiring the characteristics of the subject's eye and an imaging for acquiring an image of the subject's eye. Examples of the objective measurement include objective refractometry, corneal shape measurement, tonometry, fundus imaging, OCT measurement, and the like.

The ophthalmologic apparatus according to some embodiments is capable of performing objective measurement and subjective inspection. The subjective inspection is a method for measurement to acquire information using the responses from the subject. Examples of the subjective inspection include a visual field test, and subjective refractometry such as a far vision test, a near vision test, a contrast test, a glare test and the like.

Hereinafter, a fundus conjugate position is a position substantially optically conjugate with a fundus of a subject's eye in a state where alignment is completed, and means a position optically conjugate with the fundus of the subject's eye or the vicinity of the position. Similarly, a pupil conjugate position is a position substantially optically conjugate with a pupil of a subject's eye in a state where alignment is completed, and means a position optically conjugate with the pupil of the subject's eye or the vicinity of the position.

<Configuration of the Optical System>

FIG. 1 illustrates an example of the configuration of an optical system of the ophthalmologic apparatus according to the embodiments. The ophthalmologic apparatus 1000 according to the embodiments includes a refractometry optical system (refractive power measurement optical system) and an OCT optical system as an optical system for performing inspection for a subject' eye, and is configured to separate an optical path of the OCT optical system from an optical path of the refractometry optical system by performing wavelength separation with an optical filter.

The ophthalmologic apparatus 1000 includes a Z alignment system 1, a XY alignment system 2, a keratometry system 3, a fixation projection system 4, an anterior segment observation system 5, a refractometry projection system 6, a refractometry light reception system 7, and an OCT optical system 8. Hereinafter, for example, it is assumed that light with 940 nm to 1000 nm is mainly used in the anterior segment observation system 5, light with 830 nm to 880 nm is used in the refractometry optical system (refractometry projection system 6, refractometry light reception system 7), light with 400 nm to 700 nm is used in the fixation projection system 4, and light with 840 nm (center wavelength) is used in the OCT optical system 8.

(Anterior Segment Observation System 5)

The anterior segment observation system 5 is configured to acquire a moving image of an anterior segment of the subject's eye E. In an optical system passing through the anterior segment observation system 5, an imaging plane of an imaging element 59 is arranged at the pupil conjugate position. An anterior segment illumination light source 50 irradiates illumination light (for example, infrared light) on the anterior segment of the subject's eye E. The light reflected from the anterior segment of the subject's eye E passes through an objective lens 51, is transmitted through a dichroic mirror 52, passes through the aperture part formed in a diaphragm (telecentric diaphragm) 53, is transmitted through a half mirror 23, passes through relay lenses 55 and 56, and is transmitted through a dichroic mirror 76. The light transmitted through the dichroic mirror 76 forms an image on an imaging surface of the imaging element 59 (area sensor) by an imaging lens 58. The imaging element 59 performs an imaging and a signal outputting at a predetermined rate. The output (video signal) of the imaging element 59 is input to a processing unit (processor) 9 described after. The processing unit 9 displays an anterior segment image E' based on this video signal on a display screen 10a of a display unit 10 described after. The anterior segment image E' is an infrared moving image for example.

(Z Alignment System 1)

The Z alignment system 1 is configured to project light (infrared light) for performing alignment in an optical axis direction (front-back directions, Z direction) of the anterior segment observation system 5 onto the subject's eye E. Light emitted from a Z alignment light source 11 is projected onto a cornea Cr of the subject's eye E, is reflected by the cornea Cr, and forms an image on a line sensor 13 by an imaging lens 12. When the position of the corneal apex changes in the optical axis direction of the anterior segment observation system 5, the projection position of the light onto the line sensor 13 changes. The processing unit 9 specifies a position of the corneal apex of the subject's eye E based on the projection position of the light onto the line sensor 13 and controls a mechanism for moving the optical system to perform Z alignment based on this.

(XY Alignment System 2)

The XY alignment system 2 is configured to project light (infrared light) for performing alignment in a direction (left-right directions (X direction), up-down directions (Y direction)) orthogonal to the optical axis direction of the anterior segment observation system 5 onto the subject's eye E. The XY alignment system 2 includes a XY alignment light source 21 and a collimator lens 22 that are provided in an optical path branched from the optical path of the anterior segment observation system 5 by the half mirror 23. The light emitted from the XY alignment light source 21 passes through the collimator lens 22, is reflected by the half mirror 23, and is projected onto the subject's eye E through the anterior segment observation system 5. Reflected light from the cornea Cr of the subject's eye E is guided to the imaging element 59 through the anterior segment observation system 5.

An image (bright spot image) Br based on the reflected light is included in the anterior segment image E'. The processing unit 9 controls the display unit to display an alignment mark AL and the anterior segment image E' including the bright spot image Br on the display screen of the display unit. In the case of performing XY alignment manually, a user can perform an operation for moving the optical system so as to guide the bright spot image Br in the alignment mark AL. In the case of performing XY alignment automatically, the processing unit 9 controls a mechanism for moving the optical system so as to cancel a displacement of the bright spot image Br with respect to the alignment mark AL.

(Keratometry System 3)

The keratometry system 3 is configured to project a ring-shaped light flux (infrared light) for measuring a shape of the cornea Cr of the subject's eye E onto the cornea Cr. A kerato plate 31 is disposed between the objective lens 51 and the subject's eye E. A kerato-ring light source 32 is provided on the back side (the objective lens 51 side) of the kerato plate 31. By illuminating the kerato plate 31 with light from the kerato-ring light source 32, the ring-shaped light flux is projected onto the cornea Cr. The reflected light (kerato-ring image) from the cornea Cr of the subject's eye E is detected by the imaging element 59 along with the anterior segment image E'. The processing unit 9 calculates a corneal shape parameter representing a shape of the cornea Cr, by performing a known calculation based on this kerato-ring image.

(Refractometry Projection System 6 and Refractometry Light Reception System 7)

The refractometry optical system includes the refractometry projection system 6 and the refractometry light reception system 7 which are used for refractive power measurement. The refractometry projection system 6 is configured to project light flux (a ring-shaped light flux, for example) (infrared light) for measuring refractive power onto the fundus Ef. The refractometry light reception system 7 is configured to receive returning light of the light flux from the subject's eye E. The refractometry projection system 6 is provided in an optical path branched by the perforated prism 65 provided in an optical path of the refractometry light reception system 7. A hole part formed in the perforated prism 65 is arranged at the pupil conjugate position. In an optical system passing through the refractometry light reception system 7, the imaging surface of the imaging element 59 is arranged at the fundus conjugate position.

In some embodiments, the refractometry light source 61 is a SLD (Super Luminescent Diode) light source which is a high-intensity light source. The refractometry light source 61 is movable in an optical axis direction. The refractometry light source 61 is arranged at the fundus conjugate position. The light emitted from the refractometry light source 61 passes through the relay lens 62 and is incident on a conical surface of the conical prism 63. The light incident on the conical surface is deflected and emits from a bottom surface of the conical prism 63. The light emitted from the bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by a filter 70. As described after, the filter 70 is an optical element for separating the optical path of the OCT optical system from the optical path of the refractometry optical system by performing wavelength separation. The light reflected by the filter 70 is reflected by the dichroic mirror 52, passes through the objective lens 51, and is projected onto the subject's eye E. The rotary prism 66 is used for averaging the light quantity distribution of the ring-shaped light flux with respect to the blood vessel or the diseased site of the fundus Ef or for reducing the speckle noise caused by the light source.

Returning light of the ring-shaped light flux projected onto the fundus Ef passes through the objective lens 51, and is reflected by the dichroic mirror 52 and the filter 70. The returning light reflected by the filter 70 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by a dichroic mirror 76, and forms an image on the imaging surface of the imaging element 59 by the imaging lens 58. The processing unit 9 calculates a refractive power value of the subject's eye E by performing the known calculation based on the output of the imaging element 59. For example, the refractive power value includes spherical power, astigmatic power, and astigmatic axis angle.

(Fixation Projection System 4)

The OCT optical system 8 described after is provided in an optical path wavelength—separated from the optical path of the refractometry optical system by the filter 70. The fixation projection system 4 is provided in an optical path branched from the optical path of the OCT optical system 8 by the dichroic mirror 83.

The fixation projection system 4 is configured to present a fixation target to the subject's eye E. Under the control of the processing unit 9, a liquid crystal panel 41 displays a pattern representing the fixation target. By changing the display position of the fixation target on the screen of the liquid crystal panel 41, the fixation position of the subject's eye E can be changed. Examples of the fixation position of the subject's eye E include a position for acquiring an image centered at a macular region of the fundus Ef, a position for acquiring an image centered at an optic disc, and a position for acquiring an image centered at the fundus center between the macular region and the optic disc. The display position of the pattern representing the fixation target can be arbitrarily changed.

The light from the liquid crystal panel 41 passes through a relay lens 42, is transmitted through the dichroic mirror 83, passes through a relay lens 82, is reflected by a reflective mirror 81, is transmitted through the filter 70, and is reflected by the dichroic mirror 52. The light reflected by the dichroic mirror 52 passes through the objective lens 51 and is projected onto a fundus Ef. The liquid crystal panel 41 (or the liquid crystal panel 41 and the relay lens 42) is movable in the optical axis direction.

(OCT Optical System 8)

The OCT optical system 8 is an optical system for performing OCT measurement. The position of the focusing lens 87 is adjusted so that an end face of an optical fiber fl and the fundus Ef are optically conjugate with each other based on the result of the refractometry performed before the OCT measurement.

The OCT optical system 8 is provided in the optical path wavelength-separated from the optical path of the refractometry optical system by the filter 70. The optical path of the above fixation projection system 4 is coupled with the optical path of the OCT optical system 8 by the dichroic mirror 83. Thereby, the optical axes of the OCT optical system 8 and the fixation projection system 4 can be coupled coaxially.

Figure 2:
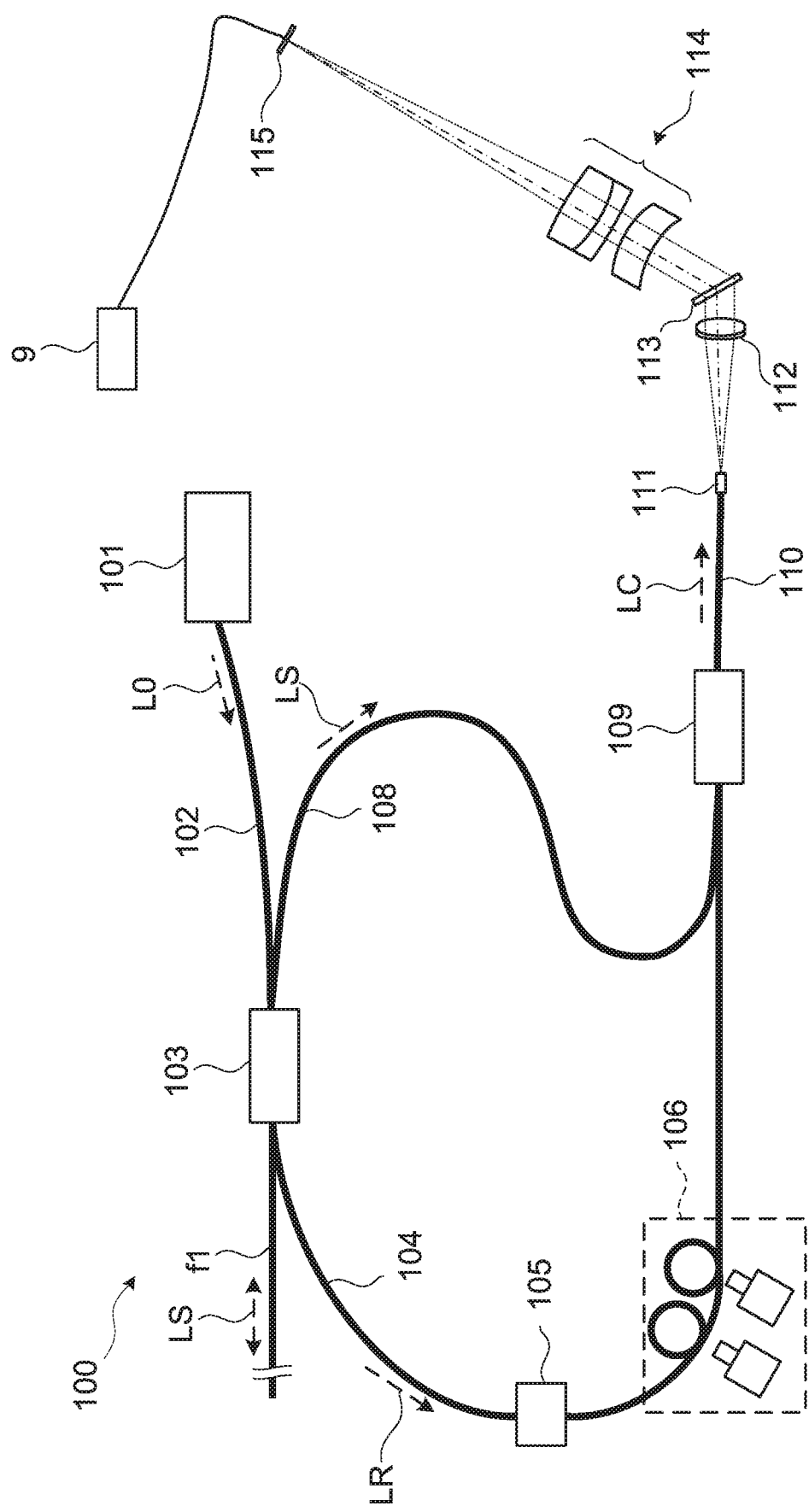
FIG. 2 is a schematic diagram illustrating an example of a configuration of an optical system of the ophthalmologic apparatus according to the embodiments.

The OCT optical system 8 includes an OCT unit 100. As shown in FIG. 2, the OCT unit 100 is configured to split low-coherence light into reference light and measurement light, make the measurement light having passed through the subject's eye E (fundus Ef) and the reference light having traveled through a reference optical path interfere with each other to generate interference light, and detect the spectral component of the interference light. The result of the detection (detection signal) is sent to the processing unit 9.

In the OCT unit 100, an OCT light source 101 includes a low-coherence light source as with the general spectral domain type OCT apparatus. The OCT light source 101 outputs broadband, low-coherence light L0. The low-coherence light L0 includes, for example, a near-infrared region (the center wavelength is 830$nm$ and the wavelength range is approximately 800 nm to 900 nm), and a temporal coherence length of around several tens of micrometers. The OCT light source unit 101 includes a light output device, such as a super luminescent diode (SLD), an LED, a semiconductor optical amplifier (SOA), or the like.

The low coherence light L0 output from the OCT light source 101 is guided through an optical fiber 102 to a fiber coupler 103, and divided into the measuring light LS and the reference light LR.

The reference light LR is guided through an optical fiber 104 and arrives at an optical attenuator 105. The optical attenuator 105 automatically adjusts the amount of the reference light LR guided through the optical fiber 104 under the control of the processing unit 9 using a known technology. The reference light LR whose light amount having adjusted by the optical attenuator 105 is guided through the optical fiber 104 and arrives at a polarization adjuster (polarization controller) 106. The polarization adjuster 106 is a device that applies external stress to the looped optical fiber 104 to thereby adjust the polarization condition of the reference light LR guided through the optical fiber 104. Note that the configuration of the polarization adjuster 106 is not limited to this and any known technologies can be used. The reference light LR whose polarization condition has been adjusted by the polarization adjuster 106 arrives at a fiber coupler 109.

The measurement light LS generated by the fiber coupler 103 is guided through an optical fiber fl, passes through an optical path length changing unit 89, and is collimated into a parallel light flux by the collimator lens 90 in FIG. 1. The optical path length changing unit 89 changes an optical path length of the measurement light LS. Further, the measurement light LS arrives at the dichroic mirror 83 via an optical scanner 88, the focusing lenses 86 and 85, and the reflective mirror 84. The optical scanner 88 deflects the measurement light LS in a one-dimensionally or two-dimensional manner. The optical scanner 88 includes a first galvano mirror and a second galvano mirror, for example. The first galvano mirror deflects the measurement light LS so as to scan the fundus Ef in a horizontal direction orthogonal to the optical axis of the OCT optical system 8. The second galvano mirror deflects the measurement light LS deflected by the first galvano mirror so as to scan the fundus Ef in a vertical direction orthogonal to the optical axis of the OCT optical system 8. Examples of scan modes with the measurement light LS performed by the optical scanner 88 like this include horizontal scan, vertical scan, cross scan, radial scan, circle scan, concentric scan, helical (spiral) scan, and the like.

The measurement light LS is reflected by the dichroic mirror 83, passes through the relay lens 82, is reflected by the reflective mirror 81, is transmitted through the filter 70, and is reflected by the dichroic mirror 52. The measurement light LS reflected by the dichroic mirror 52 is refracted by the objective lens 51 and is irradiated on the fundus Ef, for example. The measurement light LS is scattered and reflected at various depth positions of the fundus Ef. Backscattered light of the measurement light LS from the fundus Ef reversely advances along the same path as the outward path, and is guided to the fiber coupler 103. Then, the back-scattered light passes through an optical fiber 108, and arrives at the fiber coupler 109.

The fiber coupler 109 causes the back-scattered light of the measurement light LS and the reference light LR having passed through the optical fiber 104 to interfere with each other. Interference light LC thus generated is guided through an optical fiber 110 and output from an exit end 111. The interference light LC is collimated into a parallel light flux by a collimator lens 112, is spectrally divided (spectrally decomposed) by a diffraction grating 113, is converged by a convergence lens 114, and is projected onto a light receiving surface of a detector 115 such as CCD image sensor. Note that although FIG. 2 illustrates the diffraction grating 113 of the transmission type, it is possible to use a spectrally decomposing element of any other type, such as a diffraction grating of reflection type.

The detector 115 is, for example, a line sensor, and detects the spectral components of the interference light LC to convert them to electric charges. The detector 115 accumulates the electric charges to generate a detection signal, and sends the detection signal to the processing unit 9.

Although a Michelson interferometer is employed in this embodiment, it is possible to employ any type of interferometer such as Mach-Zehnder-type as appropriate. Instead of the CCD image sensor as the detector 115, another type of image sensor, such as a complementary metal-oxide semiconductor (CMOS) image sensor, can be used.

The processing unit 9 calculates the refractive power value from the result of the measurement obtained by using the refractometry optical system, and controls the refractometry light source 61 and the focusing lens 74 to move respectively to positions where the fundus Ef, the refractometry light source 61, and the imaging element 59 are conjugate with each other, in the optical axis direction based on the calculated refractive power value. In some embodiments, the processing unit 9 controls the liquid crystal panel 41 to move in its optical axis direction in conjunction with the movement of the refractometry light source 61 and the focusing lens 74. In some embodiments, the processing unit 9 controls the focusing lens 87 of the OCT optical system 8 to move in its optical axis direction in conjunction with the movement of the focusing lens 74.

As described above, the OCT optical system 8 is provided in the optical path wavelength-separated from the optical path of the refractometry optical system by the filter 70. That is, the inspection optical system provided in the optical path wavelength-separated from the optical path of the refractometry optical system by the filter 70 includes an interference optical system. The interference optical system is configured to split the light in a predetermined wavelength range from a light source into reference light and measurement light, to project the measurement light onto the subject's eye, and to detect the interference light between returning light of the measurement light from the subject's eye and the reference light.

For example, in the case of separating the optical path of the OCT optical system 8 from the optical path the refractometry optical system by using a perforated prism, it is necessary to consider vignetting of the measurement light or the returning light thereof and the like, since the optical system is configured to allow the measurement light to pass through the hole part of the perforated prism. On the other hand, by performing wavelength separation by using the filter 70, the light amount of the light used in each optical system can be increased compared with using the perforated prism.

The filter 70 is an optical filter capable of changing its wavelength separation characteristics. The wavelength separation characteristics correspond to transmission characteristics of the wavelength of incident light or reflection characteristics of the wavelength of incident light. Examples of the wavelength separation characteristics include cut-on wavelength, cut-off wavelength, cutoff region, and the like. The filter 70 according to some embodiments is capable of changing the filter type. Examples of the filter type include a narrow band pass filter, a broad band pass filter, a short pass filter, a long pass filter, a neutral density filter, and the like. In this embodiment, the wavelength separation characteristics are changed so that the light in the wavelength range used in the refractometry and the light in the wavelength range used in the OCT measurement is wavelength-separated according to the type of inspection.

Figure 3:
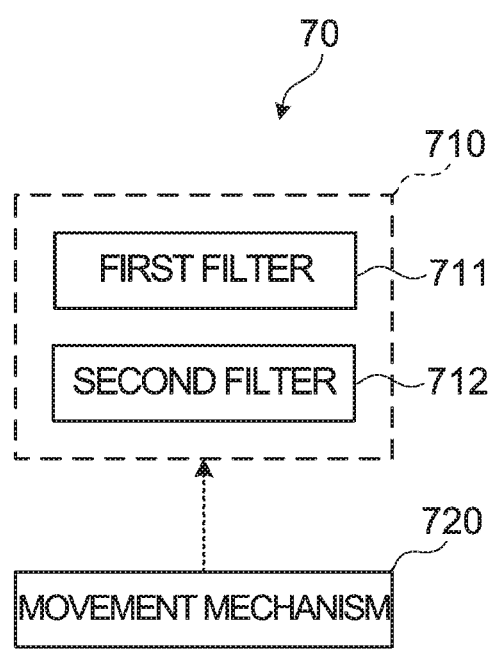
FIG. 3 is a schematic diagram illustrating an example of the configuration of the ophthalmologic apparatus according to the embodiments.
Figure 4A:
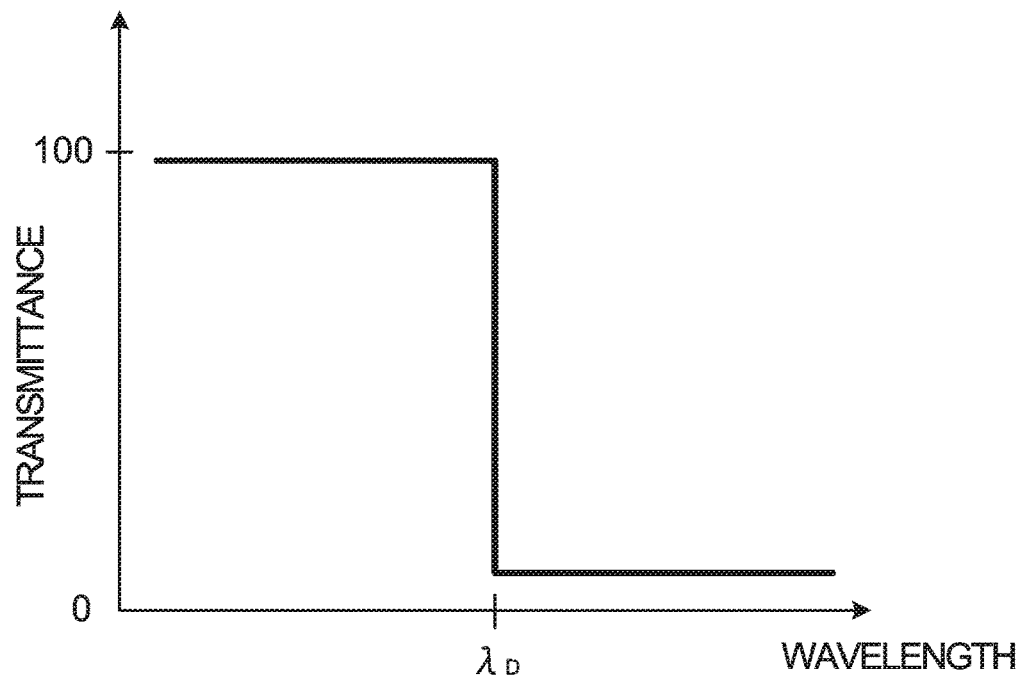
FIG. 4A is a schematic diagram illustrating an example of the configuration of the ophthalmologic apparatus according to the embodiments.
Figure 4B:
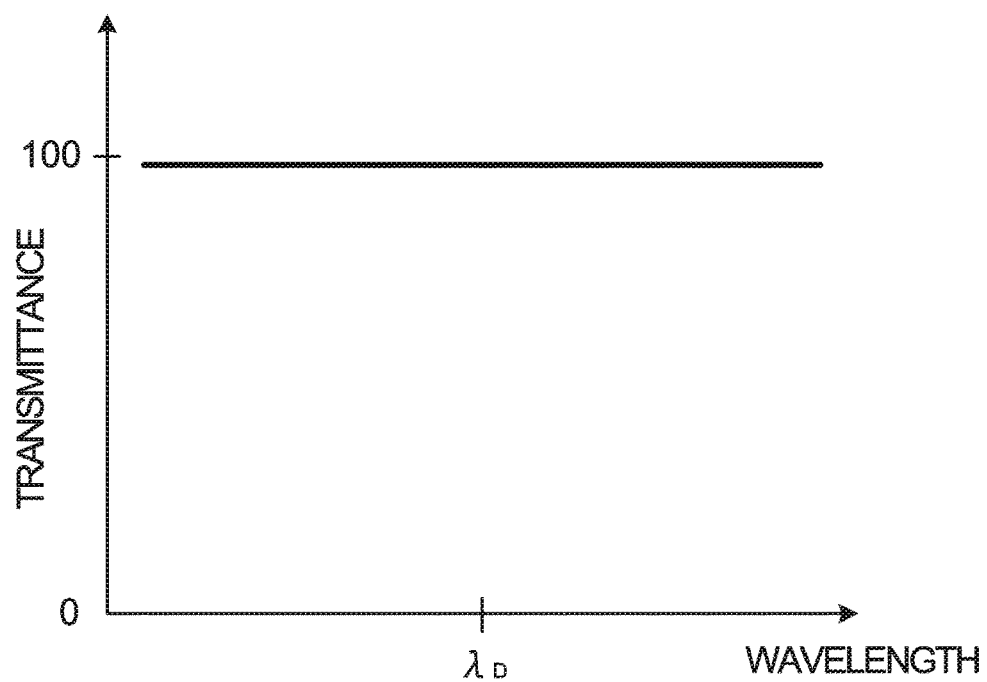
FIG. 4B is a schematic diagram illustrating an example of the configuration of the ophthalmologic apparatus according to the embodiments.

FIGS. 3, 4A, and 4B show explanatory diagrams of the filter 70 according to the embodiments. FIG. 3 shows a block diagram of an example of the configuration of the filter 70 according to the embodiments. FIG. 4A schematically shows the wavelength separation characteristics of a first filter 711 in FIG. 3. FIG. 4B schematically shows the wavelength separation characteristics of a second filter 712 in FIG. 3. In FIGS. 4A and 4B, the horizontal axis represents wavelength, while the vertical axis represents transmittance of light.

As shown in FIG. 3, the filter 70 includes a filter group 710 and a movement mechanism 720. The filter group 710 includes a plurality of filters with different wavelength separation characteristics. The movement mechanism 720 moves (rotates or translates) the plurality of filters of the filter group 710. The movement mechanism 720 moves at least one of the plurality of filters included in the filter group 710 to selectively arrange a filter in the optical path of the refractometry optical system.

In this embodiment, the filter group 710 includes the first filter 711 for refractometry and the second filter 712 for OCT measurement. When the refractometry is performed, the first filter 711 is arranged in the optical path of the refractometry optical system. When the OCT measurement is performed, the second filter 712 is arranged in the optical path of the refractometry optical system. At least one of the first filter 711 and the second filter 712 according to some embodiments is a dichroic mirror.

The first filter 711 has first wavelength separation characteristics as shown in FIG. 4A. The first wavelength separation characteristics have characteristics similar to those of a short pass filter (long wavelength cut filter) having a cut-on wavelength (cutoff wavelength) of $\lambda_D$. The first wavelength separation characteristics indicate that the shorter wavelength side than the wavelength $\lambda_D$ is the transmission wavelength region and the longer wavelength side than the wavelength $\lambda_D$ In is the reflection wavelength region. The first filter 711 has wavelength separation characteristics in which the wavelength range (400 nm to 700 nm) of the light used in the fixation projection system 4 is the transmission wavelength region and the wavelength range (830 nm to 880 nm) of the light used in the refractometry optical system is the reflection wavelength region. That is, the wavelength range of the light used in the OCT optical system 8 is included in the reflection wavelength region.

The second filter 712 has second wavelength separation characteristics different from the first wavelength separation characteristics, as shown in FIG. 4B. The second wavelength separation characteristics indicate that the entire region of the wavelength region is the transmission wavelength region. The second filter 712 has wavelength separation characteristics (wavelength transmission characteristics) in which the wavelength range (400 nm to 700 nm) of the light used in the fixation projection system 4 and the wavelength range (830 nm to 880 nm) of the light used in the refractometry optical system are the transmission wavelength range.

In some embodiments, the first filter 711 and the second filter 712 are held by a holding member (not shown) in a cross direction with respect to the optical path of the refractometry optical system. The movement mechanism 720 moves the holding member in the cross direction to selectively arrange the first filter 711 and the second filter 712 in the optical path of the refractometry optical system.

In some embodiments, the first filter 711 and the second filter 712 are held in a circumferential direction of a turret plate (not shown). The turret plate is rotatable around a rotation axis substantially parallel to the optical path (optical axis) of the refractometry optical system. The first filter 711 and the second filter 712 are arranged on the circumference of the turret plate, through which the optical path of the refractometry optical system passes, around the rotation axis. The movement mechanism 720 rotates the turret plate around the rotation axis to selectively arrange the first filter 711 and the second filter 712 in the optical path of the refractometry optical system.

As described above, by changing the wavelength separation characteristics of the filter 70 according to the type of inspection (content of inspection), it is possible to suppress loss of light amount and to perform inspection and measurement with high-precision while simplifying the configuration in each of the refractometry and the OCT measurement.

<Configuration of Processing System>

Figure 5:
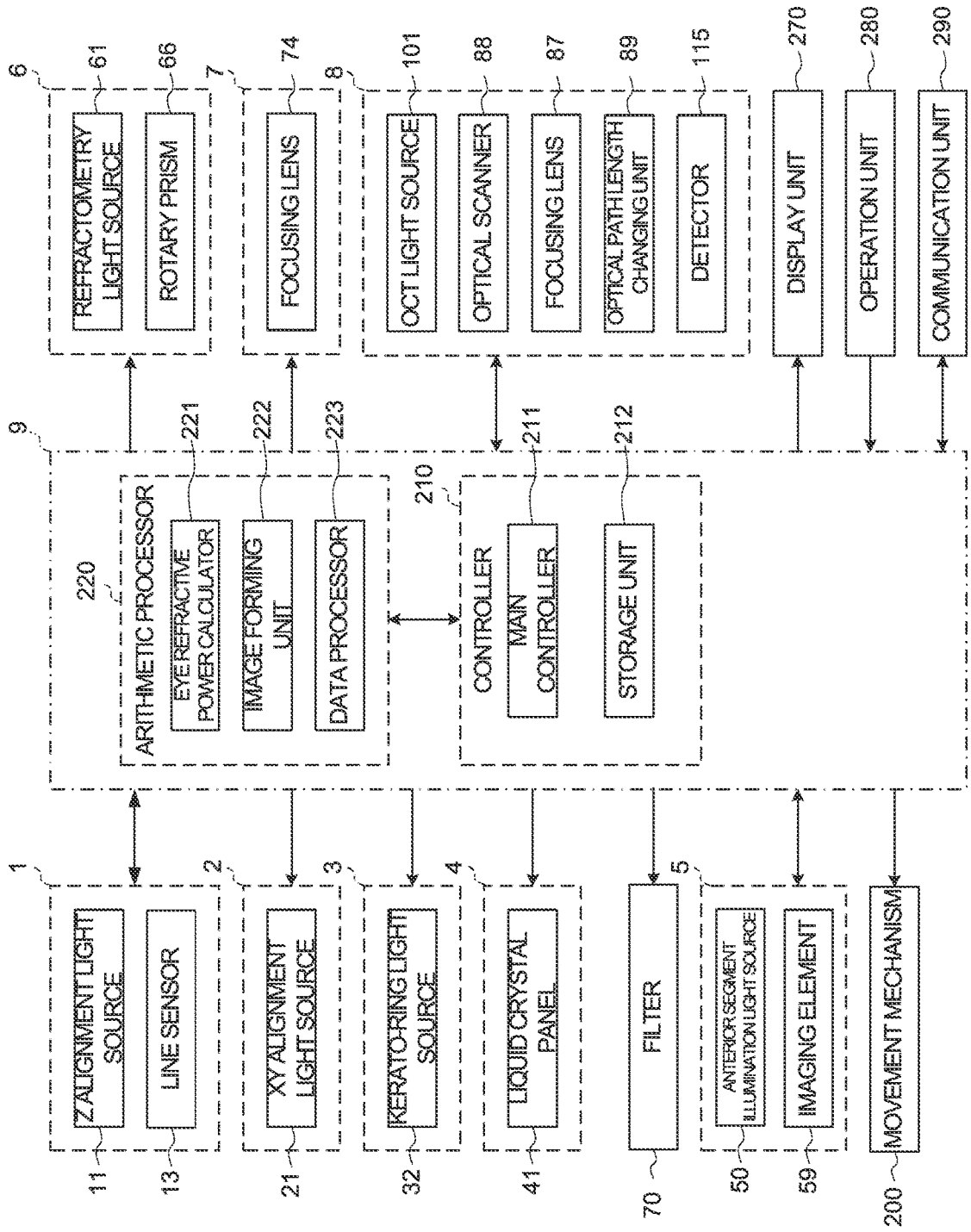
FIG. 5 is a schematic diagram illustrating an example of a configuration of a processing system of the ophthalmologic apparatus according to the embodiments.

The processing system of the ophthalmologic apparatus 1000 will be described. FIG. 5 illustrates an example of the functional structure of the processing system of the ophthalmologic apparatus 1000. FIG. 5 shows an example of a functional block diagram illustrating the processing system of the ophthalmologic apparatus 1000.

The processing unit 9 controls each part of the ophthalmologic apparatus 1000. Further, the processing unit 9 is capable of performing various types of arithmetic processing. The processing unit 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processing unit 9 realizes the function according to the embodiments, for example, by read out a computer program stored in a storage circuit or a storage device and executing the computer program.

The processing unit 9 includes a controller 210 and an arithmetic processor 220. Further, the ophthalmologic apparatus 1000 includes a movement mechanism 200, a display unit 270, an operation unit 280, and a communication unit 290.

The movement mechanism 200 is a mechanism for moving a head unit in front, back, left and right directions, the head unit housing the optical systems such as the Z alignment system 1, the XY alignment system 2, the keratometry system 3, the fixation projection system 4, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

(Controller 210)

The controller 210 includes a processor and controls each part of the ophthalmologic apparatus. The controller 210 includes the main controller 211 and a storage unit 212. The storage unit 212 stores, in advance, a computer program for controlling the ophthalmologic apparatus. The computer program includes light source control programs, detector control programs, optical scanner control programs, optical system control programs, arithmetic processing programs, programs for user interface, and the like. The main controller 211 operates according to the computer programs, and thereby the controller 210 performs the control processing.

The main controller 211 performs various controls of the ophthalmologic apparatus, as a measurement controller. Examples of control of the Z alignment system 1 include control of the Z alignment light source 11, control of the line sensor 13, and the like. Examples of the control of the Z alignment light source 11 include turning on and off of the light source, adjustment of amount of light, adjustment of aperture, and the like. Examples of the control of the line sensor 13 include adjustment of exposure of a detecting element, adjustment of gain of a detecting element, adjustment of detecting rate of a detecting element, and the like. Thereby, the Z alignment light source 11 can be switched between lighting and non-lighting or light amount can be changed. The main controller 211 acquires a signal detected by the line sensor 13 and specifies the projection position of light onto the line sensor 13 based on the acquired signal. The main controller 211 specifies a position of a corneal apex of the subject's eye E based on the specified projection position and controls the movement mechanism 200 based on the specified position to move the head unit in front and back directions (Z alignment).

Examples of control of the XY alignment system 2 include control of the XY alignment light source 21, and the like. Examples of the control of the XY alignment light source 21 include turning on and off of the light source, adjustment of amount of light, adjustment of aperture, and the like. Thereby, the XY alignment light source 21 can be switched between lighting and non-lighting, or light amount can be changed. The main controller 211 acquires a signal detected by the imaging element 59, and specifies a position of a bright spot image on the basis of returning light of the light from the XY alignment light source 21 based on the acquired signal. The main controller 211 controls the movement mechanism 200 to move the head unit in left, right, up, down directions so as to cancel a displacement the position of the bright spot image with respect to a predetermined target position (for example, a center position of the alignment mark AL) (XY alignment).

Examples of control for the keratometry system 3 include control of the kerato-ring light source 32, and the like. Examples of the control of the kerato-ring light source 32 include turning on and off of the light source, adjustment of light amount, adjustment of aperture, and the like. Thereby, the kerato-ring light source 32 can be switched between lighting and non-lighting, or light amount can be changed. The main controller 211 controls the arithmetic processor 220 to perform a known calculation on a kerato-ring image detected by the imaging element 59. Thereby, corneal shape parameters of the subject's eye E are obtained.

Examples of control for the fixation projection system 4 include control of the liquid crystal panel 41 and the like. Examples of the control of the liquid crystal panel 41 include displaying on and off of the visual targets, switching the display position of the fixation target, and the like. Thereby, the fixation target is projected onto the fundus Ef of the subject's eye E. For example, the fixation projection system 4 includes a movement mechanism that moves the liquid crystal panel 41 (or the liquid crystal panel 41 and the relay lens 42) in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move at least the liquid crystal panel 41 in the optical axis direction. Thereby, the position of liquid crystal panel 41 is adjusted so that the liquid crystal panel 41 and the fundus Ef are optically conjugate with each other.

Examples of control of the filter 70 include control of changing the wavelength separation characteristics of the filter 70 and the like. In particular, the main controller 211 controls the movement mechanism 720 shown in FIG. 3 according to the type of inspection to selectively arrange the first filter 711 and the second filter 712 in the optical path of the refractometry optical system.

In some embodiments, upon reception of an instruction of turning on the refractometry light source 61, the main controller 211 controls the filter 70 to automatically arrange the first filter 711 in the optical path of the refractometry optical system. In this case, the main controller 211 may automatically perform control of turning off the OCT light source 101.

In some embodiments, upon reception of an instruction of turning on the OCT light source 101, the main controller 211 controls the filter 70 to automatically arrange the second filter 712 in the optical path of the refractometry optical system. In this case, the main controller 211 may automatically perform control of turning off the refractometry light source 61.

Examples of the control for the anterior segment observation system 5 include control of an anterior segment illumination light source 50, control of the imaging element 59, and the like. Examples of control of the anterior segment illumination light source 50 include turning on and off the light source, adjustment of light amount, adjustment of aperture, and the like. Thereby, the anterior segment illumination light source 50 can be switched between lighting and non-lighting, or light amount can be changed. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of control for the refractometry projection system 6 include control of the refractometry light source 61, control of the rotary prism 66, and the like. Examples of the control of the refractometry light source 61 include turning on and off of the light source, adjustment of light amount, adjustment of aperture, and the like. Thereby, the refractometry light source 61 can be switched between lighting and non-lighting, or light amount can be changed. For example, the refractometry projection system 6 includes a movement mechanism that moves the refractometry light source 61 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the refractometry light source 61 in the optical axis direction. Examples of the control of the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 respectively depending on the refractive power of the subject's eye E for example so that the refractometry light source 61 and the fundus Ef and the imaging element 59 are optically conjugate with each other.

Examples of control of the OCT optical system 8 include control of the OCT light source 101, control of the optical path length changing unit 89, control of the optical scanner 88, control of the focusing lens 87, control of the detector 115, and the like. Examples of the control of the OCT light source 101 includes turning on and off of the light source, adjustment of light amount, adjustment of aperture, and the like. The optical path length changing unit 89 includes, for example, a corner cube and a mechanism for moving the corner cube. The corner cube reflects the incident light parallel to the incident direction and in the direction opposite to the incident direction. The movement mechanism moves the corner cube along an optical path of the incident light. Examples of the control of the optical path length changing unit 89 include control of the movement mechanism and the like. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the corner cube along the optical path of the incident light. Examples of the control of the optical scanner 88 include control of the scanning position and the scanning area and the scanning speed by means of the first galvano mirror, control of the scanning position and the scanning area and the scanning speed by means of the second galvano mirror, and the like. Examples of the control of the focusing lens 87 include control of moving the focusing lens 87 in the optical axis direction. For example, the OCT optical system 8 include a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction. For example, the main controller 211 may moves the focusing lens 87 alone based on the intensity of the interference signal, after moving the focusing lens 87 in conjunction with the movement of the focusing lens 74. Examples of the control of the detector 115 include adjustment of exposure of a detecting element, adjustment of gain of a detecting element, adjustment of detecting rate of a detecting element, and the like. The main controller 211 performs sampling of the signal detected by the detector 115 and controls the arithmetic processor 220 (an image forming unit 222) to perform processing such as forming image based on the sampled signal and the like.

In some embodiments, the OCT optical system 8 includes an optical path length changing unit that changes an optical path length of the reference light LR. The main controller 211 controls the optical path length changing unit to change the optical path length of the reference light LR.

Further, the main controller 211 performs a process of writing data in the storage unit 212 and a process of retrieving data from the storage unit 212.

(Storage Unit 212)

The storage unit 212 stores various types of data. Examples of the data stored in the storage unit 212 include a measurement result of the objective measurement, image data of a tomographic image, image data of a fundus image, subject's eye information, and the like. The subject's eye information includes information on the subject such as patient ID and name, and information on the subject's eye such as identification information of the left eye/right eye. The storage unit 212 further stores various types of programs and data to run the ophthalmologic apparatus.

(Arithmetic Processor 220)

The arithmetic processor 220 includes an eye refractive power calculator 221, the image forming unit 222, and a data processor 223.

The eye refractive power calculator 221 analyzes a ring image (pattern image) acquired by receiving the returning light of the ring-shaped light flux (ring-shaped measurement pattern) projected onto the fundus Ef by the refractometry projection system 6 by the imaging element 59. For example, the eye refractive power calculator 221 obtains a position of the center of gravity of the ring image from the brightness distribution in the image representing the acquired ring image, obtains brightness distributions along a plurality of scanning directions extending radially from the position of the center of gravity, and specifies a ring image from this brightness distributions. Subsequently, the eye refractive power calculator 221 obtains an approximate ellipse of the specified ring image and obtains a spherical power, an astigmatic power, and an astigmatic axis angle by assigning a major axis and a minor axis of the approximate ellipse to a known formula. Alternatively, the eye refractive power calculator 221 can obtain the eye refractive power parameter based on deformation and displacement of the ring image with respect to the reference pattern.

Further, the eye refractive power calculator 221 calculates a corneal refractive power, a corneal astigmatism power, and a corneal astigmatic axis angle based on the kerato-ring image acquired by the anterior segment observation system 5. For example, the eye refractive power calculator 221 calculates a corneal curvature radius of the steepest meridian and/or the flattest meridian of the anterior surface of the cornea by analyzing the kerato-ring image and calculates above parameters based on the corneal curvature radius.

The image forming unit 222 forms image data of a tomographic image of the fundus Ef based on a signal detected by the detector 115. That is, the image forming unit 222 forms the image data of the subject's eye E based on a detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The data processor 223 performs various kinds of data processing (e.g., image processing) and various kinds of analysis on a tomographic image formed, by the image forming unit 222. For example, the data processor 223 performs various correction processes such as brightness correction and dispersion correction of images. Further, the data processor 223 performs various types of image processing and analysis on images (anterior segment image, etc.) acquired using the anterior segment observation system 5.

The data processor 223 can form volume data (voxel data) of the subject's eye E by performing known image processing such as interpolation processing for interpolating pixels between tomographic images. In the case of displaying an image based on the volume data, the data processor 223 performs a rendering processing on the volume data so as to form a pseudo three-dimensional image viewed from a specific line-of-sight direction.

(Display Unit 270, Operation Unit 280)

Upon receiving control of the controller 210, the display unit 270 displays information, as a user interface unit. The display unit 270 includes the display unit 10 as illustrated in FIG. 1 and the like.

The operation unit 280 is used to operate the ophthalmologic apparatus, as the user interface unit. The operation unit 280 includes various types of hardware keys (the joystick, buttons, switches, etc.) provided in the ophthalmologic apparatus. Further, the operation unit 280 may include various kinds of software keys (buttons, icons, menus, etc.) displayed on the touch panel type display screen 10*a*.

At least part of the display unit 270 and the operation unit 280 may be integrally configured. A typical example of this is the touch-panel display screen 10*a*.

(Communication unit 290)

The communication unit 290 has the function of communicating with an external device (not shown). The communication unit 290 includes a communication interface according to the mode of communication with an external device. Examples of the external device includes an eyeglass lens measurement device for measuring the optical properties of lenses. The eyeglass lens measurement device measures the power of the eyeglass lens worn by the subject and inputs the measurement data to the ophthalmologic apparatus 1000. The external device may also be a device (reader) having the function of reading information from a recording medium or a device (writer) having the function of writing information to a recording medium. Further, the external device may be a hospital information system (HIS) server, a Digital Imaging and Communications in Medicine (DICOM) server, a doctor terminal, a mobile terminal, a personal terminal, a cloud server, or the like. The communication unit 290 may be provided in the processing unit 9, for example.

The wavelength range (for example, 830 nm to 880 nm) of the light used in the refractive power measurement by the refractometry optical system is an example of the "first wavelength range" according to the embodiments. The refractometry optical system (the refractometry projection system 6 and the refractometry light reception system 7) is an example of the "refractive power measurement optical system" according to the embodiments. The wavelength range (for example, wavelength range of about 800 nm to 900 nm where the center wavelength is 840 nm) of the light used in the OCT measurement by the OCT optical system 8 is an example of the "second wavelength range" according to the embodiments. The OCT optical system 8 is an example of the "inspection optical system" according to the embodiments. The filter 70 is an example of the "optical path separating unit" according to the embodiments. The first filter 711 and the second filter 712 are an example of the "wavelength separation elements" according to the embodiments. The fixation projection system 4 is an example of the "fixation optical system" according to the embodiments. The dichroic mirror 83 is an example of the "optical path coupling member" according to the embodiments. The optical system included in the OCT unit 100 is an example of the "interference optical system" according to the embodiments.

<Operation Example>

The operation of the ophthalmologic apparatus 1000 according to the embodiments will be described.

Figure 6:
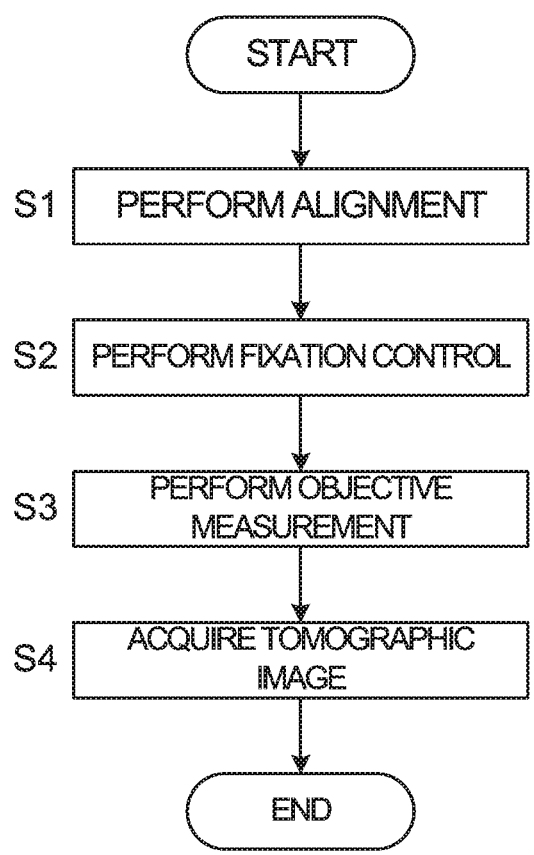
FIG. 6 is a schematic diagram illustrating a flow of the operation example of the ophthalmologic apparatus according to the embodiments.

FIG. 6 illustrates an example of the operation of the ophthalmologic apparatus 1000. FIG. 6 shows a flowchart of an example of the operation of the ophthalmologic apparatus 1000.

(S1: Perform Alignment)

When the examiner performs a predetermined operation on the operation unit 280 in a state where the face of the subject is fixed to a face supporter (not shown), the ophthalmologic apparatus 1000 performs alignment.

Specifically, the main controller 211 turns on the Z alignment light source 11 and the XY alignment light source 21. The processing unit 9 acquires imaging signal of an anterior segment image formed on the imaging surface of the imaging element 59 and controls the display unit 270 to display the anterior segment image. After that, the optical system shown in FIG. 1 is moved to at the inspection position of the subject's eye E. The inspection position is a position where the inspection of the subject's eye E can be performed with sufficient accuracy. The subject's eye E is placed at the inspection position through the alignment described above (that is, by the use of the Z alignment system 1, the XY alignment system 2, and the anterior segment observation system 5). The movement of the optical system is performed by the controller 210 according to operation or instruction from a user, or instruction by the controller 210. That is, the movement of the optical system to the inspection position of the subject's eye E and the preparation for the objective measurement are carried out.

Further, the main controller 211 moves the refractometry light source 61, the focusing lens 74, and the liquid crystal panel 41 along the respective optical axes to the origin positions (for example, the position corresponding to OD).

(S2: Perform Fixation Control)

Prior to the process of step S2, the main controller 211 controls the filter 70 to arrange the first filter 711 for refractometry in the optical path of the refractometry optical system. Thereby, the light from the fixation projection system 4 is transmitted through the filter 70 and the light used in the refractometry optical system is reflected by the filter 70.

In step S2, the main controller 211 controls the liquid crystal panel 41 to display the pattern representing the fixation target at a display position corresponding to the desired fixation position. Thereby, the subject's eye E is gazed at the desired fixation position.

Following the fixation control in step S2, the ophthalmologic apparatus 1000 may perform keratometry. In this case, the main controller 211 turns on the kerato-ring light source 32. When the light is emitted from the kerato-ring light source 32, a ring-shaped light flux for corneal shape measurement is projected onto the cornea Cr of the subject's eye E. The eye refractive power calculator 221 applies arithmetic processing to the image acquired by the imaging element 59 to calculate the corneal curvature radius. Furthermore, based on the calculated corneal curvature radius, the eye refractive power calculator 221 calculates the corneal refractive power, the corneal astigmatic power, and the corneal astigmatic axis angle. The calculated corneal refractive power and the like are stored in the storage unit 212 in the controller 210. Upon reception of an instruction from the main controller 211, an operation or instruction on the operation unit 280 by the user, the operation of the ophthalmologic apparatus 1000 proceeds to step S3.

(S3: Perform Objective Measurement)

Next, the main controller 211 controls the liquid crystal panel 41 to project the fixation target onto the subject's eye E and performs the refractometry.

In the refractometry, the main controller 211 causes a ring-shaped measurement pattern light flux for refractometry to be projected onto the subject's eye E as described above. The ring image based on the returning light of the measurement pattern light flux from the subject's eye E is imaged on the imaging surface of the imaging element 59. The main controller 211 determines whether or not the ring image based on the returning light from the fundus Ef detected by the imaging element 59 can be acquired. For example, the main controller 211 detects a position (pixel) of the edge of the image that is formed based on the returning light detected by the imaging element 59, and determines whether or not the width (difference between outer diameter and inner diameter) of the image is equal to or more than a predetermined value. Alternatively, the main controller 211 may determine whether or not the ring image can be acquired by determining whether or not a ring can be formed based on points (image) having a predetermined height (ring diameter) or more.

When it is determined that the ring image can be acquired, the eye refractive power calculator 221 analyzes the ring image based on the returning light of the measurement pattern light flux projected onto the subject's eye E by a known method, and calculates a provisional spherical power S and a provisional astigmatic power C. Based on the obtained provisional spherical power S and the obtained provisional astigmatic power C, the main controller 211 sets the refractometry light source 61, the focusing lens 74, and the liquid crystal panel 41 to respective positions of the equivalent spherical power (S+C/2) (positions corresponding to a provisional far point). The main controller 211 moves the liquid crystal panel 41 further to the fogging position from the position, and then controls the refractometry projection system 6 and the refractometry light reception system 7 to acquire a ring image again as the main measurement. The main controller 211 controls the eye refractive power calculator 221 to calculate a spherical power, an astigmatic power, and an astigmatic axis angle from the result obtained by analyzing the ring image acquired in the same manner as described above and the movement amount of the focusing lens 74.

Further, the eye refractive power calculator 221 obtains a position corresponding the far point of the subject's eye E (position corresponding to the far point obtained by the main measurement) from the obtained spherical power and the obtained astigmatic power. The main controller 211 moves the liquid crystal panel 41 to the position corresponding to the obtained far point. In the controller 210, the position of the focusing lens 74, the calculated spherical power, and the like are stored in the storage unit 212. Upon reception of an instruction from the main controller 211, an operation or instruction on the operation unit 280 by the user, the operation of the ophthalmologic apparatus 1000 proceeds to step S4.

When it is determined that the ring image can not be acquired, the main controller 211 moves the refractometry light source 61 and the focusing lens 74 to the minus power side (for example, −10D) or the plus power side (for example, +10D) in a preset step, considering the possibility of high refractive error of the eye. The main controller 211 controls the refractometry light reception system 7 to detect the ring image at each position. If it is still determined that the ring image can not be acquired, the main controller 211 executes a predetermined measurement error process. In this case, the operation of the ophthalmologic apparatus 1000 may proceed to step S4. In the controller 210, information indicating that the result of refractometry can not be acquired is stored in the storage unit 212.

As described above, the focusing lens 87 of the OCT optical system 8 is moved in the optical axis direction in conjunction with the movement of the refractometry light source 61 and the focusing lens 74.

(S4: Acquire Tomographic Image)

Prior to the process of step S4, the main controller 211 controls the filter 70 to arrange the second filter 712 for OCT measurement in the optical path of the refractometry optical system. Thereby, the light from the fixation projection system 4 and the light used in the refractometry optical system are in a state of being transmitted through the filter 70.

In step S4, the main controller 211 controls the liquid crystal panel 41 to project the fixation target onto the subject's eye E and performs the OCT measurement.

The main controller 211 turns on the OCT light source 101 and controls the optical scanner 88 so as to scan a predetermined site of the fundus Ef with the measurement light LS. A detection signal obtained by scanning with the measurement light LS is fed to the image forming unit 222. The image forming unit 222 forms a tomographic image of the fundus Ef based on the obtained detection signal. Thus, the operation of the ophthalmologic apparatus 1000 is terminated (END).

As described above, by arranging the filter 70 whose wavelength separation characteristics can be changed in the optical path of the refractometry optical system, the optical path of the OCT optical system 8 is wavelength-separated from the optical path of the refractometry optical system while switching between the wavelength separation characteristics for the refractometry and the wavelength separation characteristics for the OCT measurement. Thereby, even in the case where the wavelength range of the light used for the refractometry and the wavelength range of the light used for the OCT measurement overlap, loss of the light amount can be greatly reduced with a simple configuration and the accuracy of the refractometry and the OCT measurement can be improved.

[Modification Examples]

The configuration of the optical system of the ophthalmologic apparatus 1000 according to the embodiments is not limited to the configuration explained in FIG. 1.

<Configuration of the Optical System>

Figure 7:
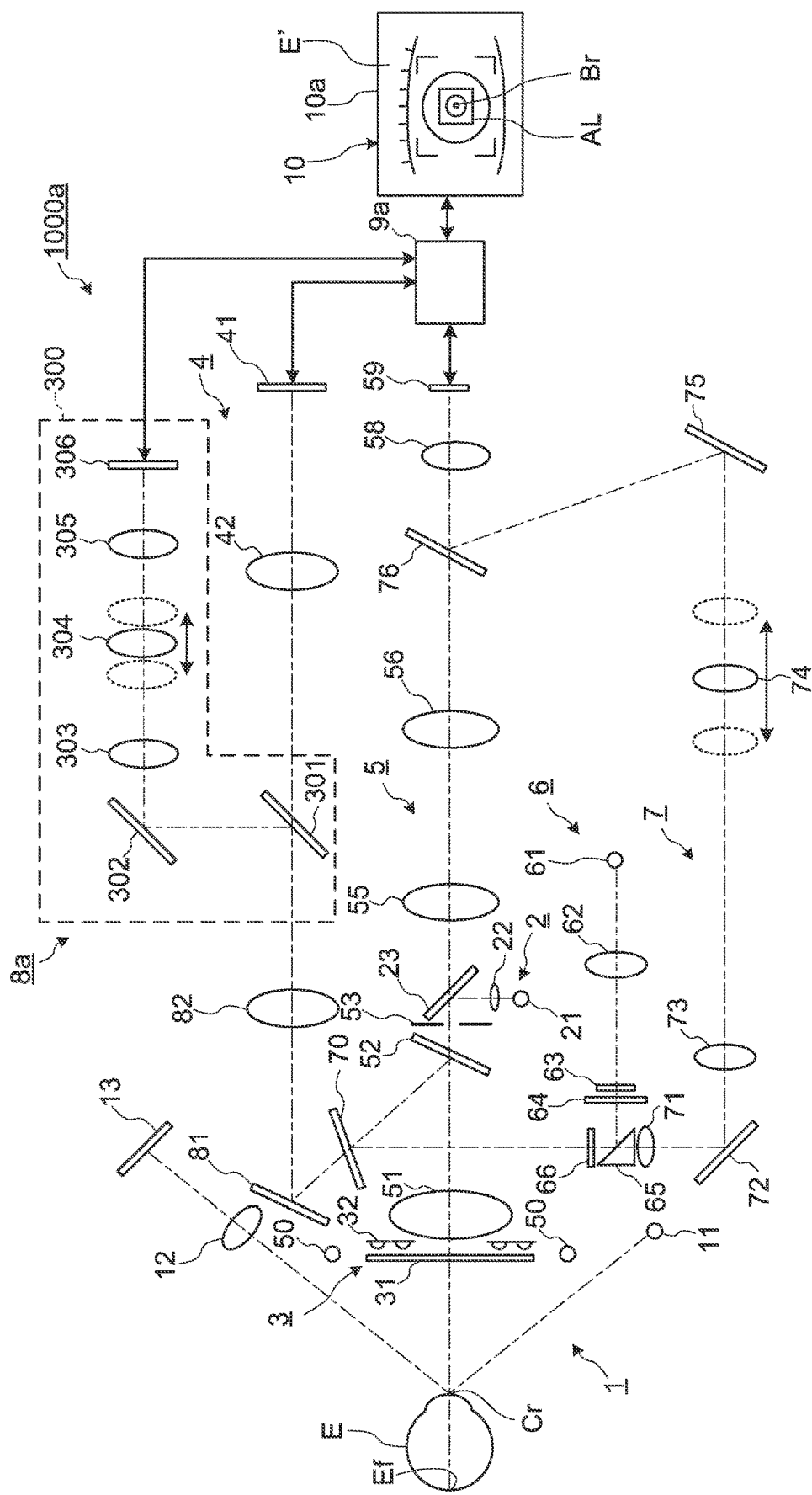
FIG. 7 is a schematic diagram illustrating an example of the configuration of an optical system of the ophthalmologic apparatus according to a modification example of the embodiments.

FIG. 7 illustrates an example of the configuration of an optical system of the ophthalmologic apparatus according to the modification example of the embodiments. In FIG. 7, parts similarly configured to those in FIG. 1 are denoted by the same reference numerals, and the description thereof is omitted unless it is necessary.

The main difference between the configuration of the ophthalmologic apparatus 1000*a* according to the modification example and the configuration of the ophthalmologic apparatus 1000 is that the inspection optical system 8*a* is provided instead of the OCT optical system 8, and that the processing unit 9*a* is provided instead of the processing unit 9. The processing unit 9*a* controls the inspection optical system 8*a*.

At least a part of the inspection optical system 8*a* is configured to be capable of replacing with another optical system for performing a different inspection or a different measurement. In particular, at least a part of the inspection optical system 8*a* is configured to be capable of replacing with an optical system included in any of two or more measurement units which are selectively attachable. The two or more measurement units include a first measurement unit and a second measurement unit. The first measurement unit includes an interference optical system that splits light from a light source into reference light and measurement light, projects the measurement light onto the subject's eye, and detects interference light between returning light of the measurement light from the subject's eye and the reference light. The second measurement unit includes a visual target projection system that projects visual target light to the subject's eye. That is, the inspection optical system 8*a* according to the embodiments is configured so that any one of the first measurement unit, which includes the optical system from the dichroic mirror 83 to the OCT unit 100 shown in FIG. 1, and the second measurement unit, which includes the optical system shown in FIG. 7, can be attached.

Therefore, when the first measurement unit is attached as shown in FIG. 1, the filter 70 performs wavelength separation of the optical path of the OCT optical system 8 from the optical path of the refractometry optical system. Further, when the second measurement unit is attached as shown in FIG. 7, the filter 70 performs wavelength separation of the optical path of the visual target projection system from the optical path of the refractometry optical system. It should be noted that when the subjective inspection is performed, the filter 70 performs wavelength separation of the optical path of the visual target projection system from the refractometry optical system with the same wavelength separation characteristics as when performing refractometry. That is, when the first measurement unit is attached, the first filter 711 is arranged in the optical path of the refractometry optical system, and even when the second measurement unit is attached, the first filter 711 is arranged in the optical path of the refractometry optical system. It should be noted that when the subjective inspection by using of the visual target projection system, the wavelength separation characteristics of the filter 70 may be changed so as to guide the visual target light to the objective lens 51.

In case that the second measurement unit 300 is attached as shown in FIG. 7 the visual target projection system projects various kinds of visual target such as a visual target for subjective inspection to the subject's eye E via the objective lens 51. A liquid crystal panel 306 displays a pattern representing a visual target under the control of the processing unit 9*a*. Light (for example, light in wavelength range of 400 nm to 700 nm, visible light) output from the liquid crystal panel 306 passes through a relay lens 305, a focusing lens 304, and a relay lens 303, is reflected by a reflective mirror 302, and is reflected by a dichroic mirror 301. The light reflected by the dichroic mirror 301 passes through the relay lens 82, is reflected by the reflective mirror 81, is transmitted through the filter 70, and is reflected by the dichroic mirror 52. The light reflected by the dichroic mirror 52 passes through the objective lens 51 and is projected onto the fundus Ef. The focusing lens 304 is movable along an optical axis of the visual target projection system. The position of the focusing lens 304 is adjusted so that the liquid crystal panel 306 and the fundus Ef are optically conjugate with each other.

As described above, the visual target projection system is provided in the optical path wavelength-separated from the optical path of the refractometry optical system by the filter 70. That is, the inspection optical system provided in the optical path wavelength-separated from the optical path of the refractometry optical system by the filter 70 includes the visual target projection system that projects the visual target light in a predetermined wavelength range onto the subject's eye.

The dichroic mirror 301 according to some embodiments is the dichroic mirror 83 shown in FIG. 1. The reflective mirror 302 according to some embodiments is the reflective mirror 84 shown in FIG. 1.

<Configuration of Processing System>

Figure 8:
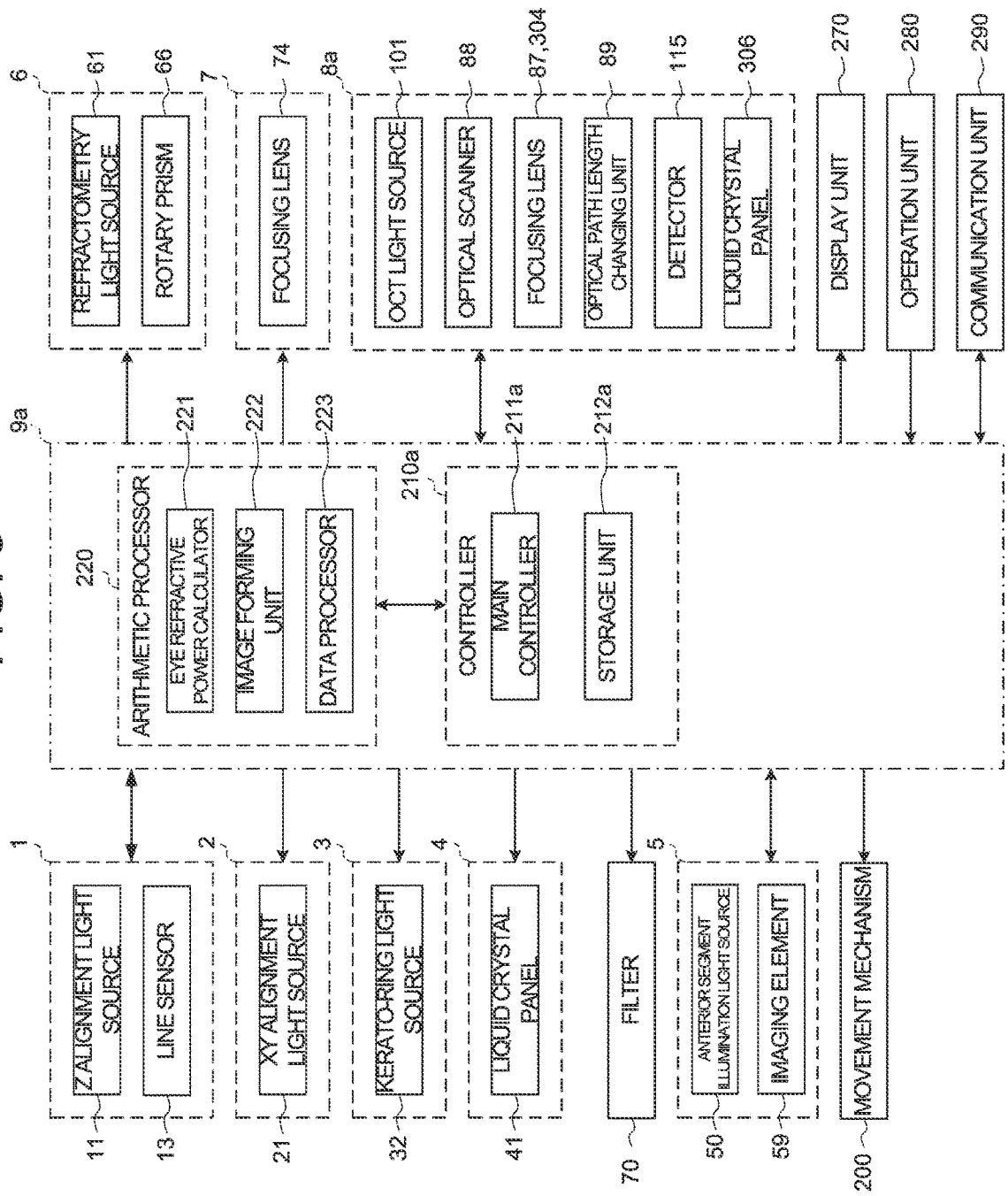
FIG. 8 is a schematic diagram illustrating an example of the configuration of a processing system of the ophthalmologic apparatus according to the modification example of the embodiments.

The processing system of the ophthalmologic apparatus 1000*a* will be described. FIG. 8 illustrates an example of the functional structure of the processing system of the ophthalmologic apparatus 1000*a*. In FIG. 8, parts similarly configured to those in FIG. 5 are denoted by the same reference numerals, and the description thereof is omitted unless it is necessary.

The processing unit 9*a* can perform control processing for the visual target projection system, in addition to processing by the processing unit 9. The processing unit 9*a* includes a controller 210*a* and the arithmetic processor 220. The controller 210*a* includes a main controller 211*a* and a storage unit 212*a*.

When the first measurement unit is attached, the main controller 211*a* controls the OCT optical system 8 as in the above embodiments. When the second measurement unit is attached, the main controller 211*a* controls the visual target projection system.

Examples of control of the visual target projection system include control of the liquid crystal panel 306, control of the focusing lens 304, and the like. Examples of the control of the liquid crystal panel 306 include displaying on and off of the visual targets, switching pattern representing the visual target, and the like. Thereby, the visual target is projected onto the fundus Ef of the subject's eye E. Examples of the control of the focusing lens 304 include control of moving the focusing lens 304 in the optical axis direction. For example, the visual target projection system includes a movement mechanism that moves the focusing lens 304 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211*a* controls the movement mechanism by sending a control signal to the actuator to move the focusing lens 304 in the optical axis direction. Thereby, the position of the focusing lens 304 is adjusted so that the liquid crystal panel 306 and the fundus Ef are optically conjugate with each other.

The visual target projection system is an example of the "subjective inspection optical system" according to the embodiments. The wavelength range (for example, 400 nm to 700 nm) of the light used in the subjective inspection by the visual target projection system is an example of the "second wavelength range" according to the embodiments.

<Operation Example>

The operation of the ophthalmologic apparatus 1000*a* according to the modification example of the embodiments will be described.

Figure 9:
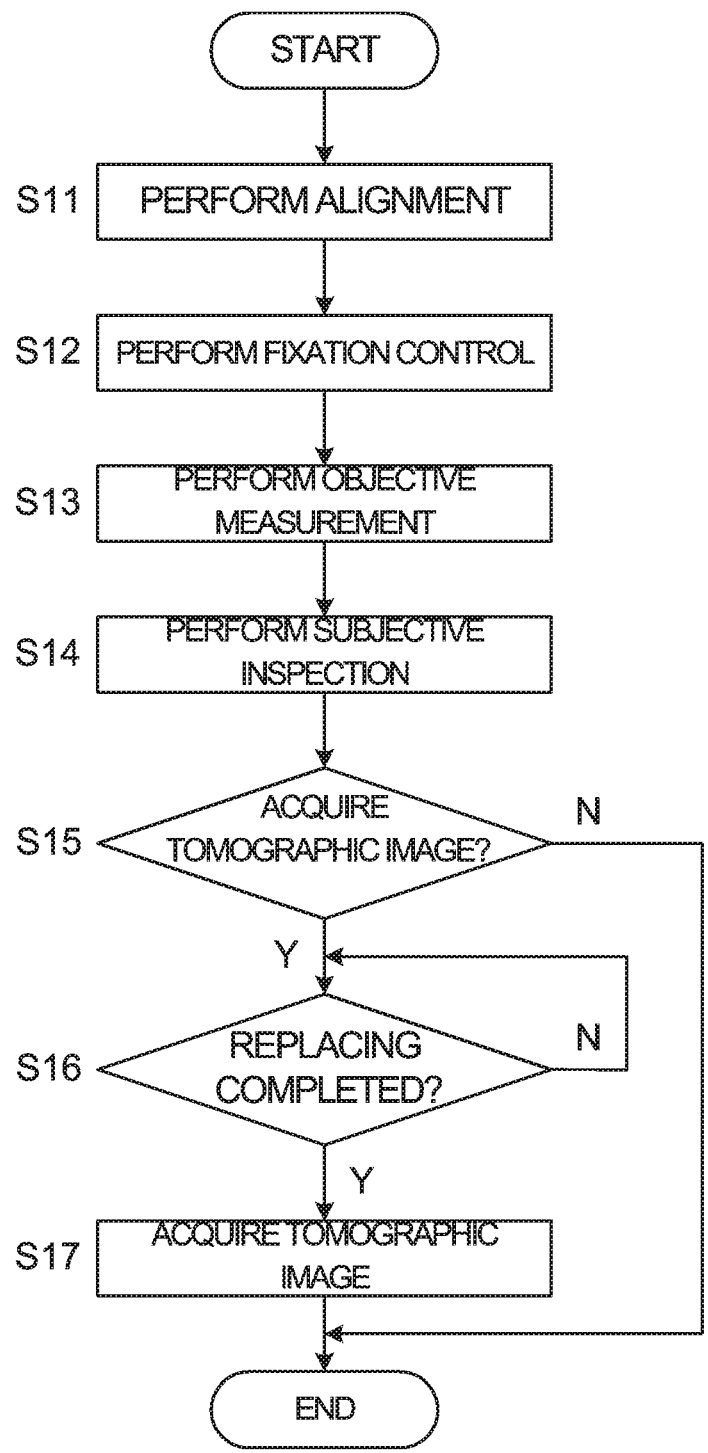
FIG. 9 is a schematic diagram illustrating a flow of the operation example of the ophthalmologic apparatus according to the embodiments.

FIG. 9 illustrates an example of the operation of the ophthalmologic apparatus 1000*a*. FIG. 9 shows a flowchart of an example of the operation of the ophthalmologic apparatus 1000*a*. In FIG. 9, it is assumed that the second measurement unit is attached in advance.

(S11: Perform Alignment)

The ophthalmologic apparatus 1000*a* performs alignment in the same manner as step S1.

(S12: Perform Fixation Control)

Prior to the process of step S12, the main controller 211*a* controls the filter 70 to arrange the first filter 711 for refractometry in the optical path of the refractometry optical system.

In step S12, the main controller 211*a* controls the liquid crystal panel 41 to display the pattern representing the fixation target at a display position corresponding to the desired fixation position, in the same manner as step S2.

Following the fixation control in step S12, the ophthalmologic apparatus 1000*a* may perform keratometry in the same manner as step S2.

(S13: Perform Objective Measurement)

Next, the main controller 211*a* controls the liquid crystal panel 41 to project the fixation target onto the subject's eye E in the same manner as step S3, and performs the refractometry.

(S14: Perform Subjective Inspection)

Subsequently, the main controller 211*a* controls the liquid crystal panel 306 to display the desired visual target based on the instruction by the user with respect to the operation unit 280, for example. Further, the main controller 211*a* moves the focusing lens 304 to a position corresponding to the result of the objective measurement. The main controller 211*a* may move the focusing lens 304 to a position corresponding to the instruction by the user with respect to the operation unit 280.

The subject submits a response with respect to the visual target projected onto the fundus Ef. For example, in the case of the visual target for the visual acuity measurement, the visual acuity value of the subject's eye is determined based on the responses from the subject. Selection of the visual target and response of the subject with respect to the selected visual target are repeatedly performed on the basis of the determination of the examiner or of the main controller 211a. The examiner or the main controller 211a determines the visual acuity values or the prescription values (S, C, A) based on the responses from the subject.

(S15: Acquire Tomographic Image?)

Next, the main controller 211a determines whether or not to acquire a tomographic image of the fundus Ef of the subject's eye E. The main controller 211a can determine whether or not to acquire the tomographic image, based on the operation contents input by the user through the operation unit 280.

When it is determined that the tomographic image is to be acquired (S15: Y), the operation of the ophthalmologic apparatus 1000a proceeds to step S16. When it is determined that the tomographic image is not to be acquired (S15: N), the ophthalmologic apparatus 1000a terminates the operation (END).

(S16: Replacing Completed?)

When it is determined that the tomographic image is to be acquired in step S15 (S15: Y), the main controller 211a determines whether or not the second measurement unit is detached and the first measurement unit is attached in the inspection optical system 8a. For example, the ophthalmologic apparatus 1000a is provided with a sensor or a microswitch for determining the attaching state of the measurement unit and the type of the attached measurement unit. The main controller 211a can specify the attaching state of the measurement unit and the type of the attached measurement unit, based on the detection result of the sensor or the state of the microswitch.

For example, the ophthalmologic apparatus 1000a waits until it is determined that replacing the measurement unit has been completed (S16: N). When it is determined that the first measurement unit is attached and replacing the measurement unit has been completed (S16: Y), the operation of the ophthalmologic apparatus 1000a proceeds to step S17.

(S17: Acquire Tomographic Image)

Prior to the process of step S17, the main controller 211a controls the filter 70 to arrange the second filter 712 for OCT measurement in the optical path of the refractometry optical system.

In step S17, the main controller 211a controls the liquid crystal panel 41 to project the fixation target onto the subject's eye E and performs the OCT measurement in the same manner as step S4. Thus, the ophthalmologic apparatus 1000a terminates the operation (END).

As described above, the inspection optical system 8a, whose optical system can be changed by replacing the measurement unit, is provided in the optical path wavelength-separated by the filter 70. Thereby, it is possible to miniaturize the ophthalmologic apparatus capable of performing the OCT measurement and the subjective inspection on the basis of the configuration of the refractometry optical system. In some embodiments, the second measurement unit includes a known optical system for performing the visual field test, and the ophthalmologic apparatus can perform the OCT measurement and the visual field test.

In the above embodiments, the case is described in which the refractometry optical system is arranged in the optical path of the light reflected by the filter 70 and the OCT optical system 8 (inspection optical system) is arranged in the optical path of the light transmitted through the filter 70. In this case, the wavelength separation characteristics of the filter 70 are changed so that when the refractometry is performed, the light in the first wavelength range is reflected and the light in the second wavelength range is transmitted, and are changed so that when the OCT measurement is performed, the light in the first wavelength is transmitted and the light in the second wavelength is transmitted.

In some embodiments, the refractometry optical system is arranged in the optical path of the light transmitted through the filter 70 and the OCT optical system 8 (inspection optical system) is arranged in the optical path of the light reflected by the filter 70. In this case, the wavelength separation characteristics of the filter 70 are changed so that when the refractometry is performed, the light in the first wavelength range is transmitted and the light in the second wavelength range is reflected, and are changed so that when the OCT measurement is performed, the light in the first wavelength is reflected and the light in the second wavelength is reflected.

[Actions and Effects]

Described below are the actions and effects of the ophthalmologic apparatus according to the embodiments or their modification examples.

An ophthalmologic apparatus (1000, 1000a) according to some embodiments includes an objective lens (51), a refractive power measurement optical system (refractometry optical system, or refractometry projection system 6 and refractometry light reception system 7), an inspection optical system (OCT optical system 8 or visual target projection system), and an optical path separating unit (filter 70). The refractive power measurement optical system is configured to project light in a first wavelength range (830 nm to 880 nm) onto a subject's eye (E) via the objective lens and to detect returning light from the subject's eye. The inspection optical system is configured to project light in a second wavelength range (wavelength range of 800 nm to 900 nm where the center wavelength is 840 nm, or 400 nm to 700 nm) onto the subject's eye via the objective lens. The optical path separating unit is arranged in an optical path of the refractive power measurement optical system and is configured to separate an optical path of the inspection optical system from the optical path of the refractive power measurement optical system by performing wavelength separation based on changeable wavelength separation characteristics.

The second wavelength range may overlap at least part of the first wavelength range (in case that the inspection optical system is the OCT optical system). Alternatively, the second wavelength range may not overlap at least part of the first wavelength range (in case that the inspection system is the subjective inspection optical system). In such a configuration, the optical path separating unit arranged in the optical path of the refractive power measurement optical system separates the optical path of the inspection optical system from the optical path of the refractive power measurement optical system by performing wavelength separation based on the changeable wavelength separation characteristics. Thereby, even in the case where at least part of the first wavelength range and the second wavelength range overlap, loss of the light amount in each optical system can be reduced and the highly accurate measurement and inspection using the refractive power measurement optical system and the inspection, optical system can be performed. In addition, by sharing the objective lens, a compact ophthalmologic apparatus on the basis of the configuration of the refractive power measurement optical system can be provided.

In the ophthalmologic apparatus according to some embodiments, the wavelength separation characteristics are changed so as to perform wavelength separation for the light in the first wavelength range and the light in the second wavelength range according to a type of inspection.

According to such a configuration, the subject's eye can be objectively measured by using the light in the first wavelength range alone in the refractive power measurement optical system and the subject's eye can be inspected by using the light in the second wavelength range alone in the inspection optical system.

In the ophthalmologic apparatus according to some embodiments, the refractive power measurement optical system is arranged in an optical path of light reflected by the optical path separating unit, and the inspection optical system is arranged in an optical path of light transmitted through the optical path separating unit. The wavelength separation characteristics are changed so that the light in the first wavelength range is reflected by the optical path separating unit and the light in the second wavelength range is transmitted through the optical path separating unit when a measurement is performed with the refractive power measurement optical system, and are changed so that the light in the first wavelength range is transmitted through the optical path separating unit and the light in the second wavelength range is transmitted through the optical path separating unit when an inspection is performed with the inspection optical system.

According to such a configuration, a compact ophthalmologic apparatus that can objectively measure the subject's eye by the refractive power measurement optical system arranged in the reflection direction of the optical path separating unit and can inspect the subject's eye by the inspection optical system arranged in the transmission direction of the optical path separating unit while sharing the objective lens can be provided.

In the ophthalmologic apparatus according to some embodiments, the refractive power measurement optical system is arranged in an optical path of light transmitted through the optical path separating unit, and the inspection optical system is arranged in an optical path of light reflected by the optical path separating unit. The wavelength separation characteristics are changed so that the light in the first wavelength range is transmitted through the optical path separating unit and the light in the second wavelength range is reflected by the optical path separating unit when a measurement is performed with the refractive power measurement optical system, and are changed so that the light in the first wavelength range is reflected by the optical path separating unit and the light in the second wavelength range is reflected by the optical path separating unit when an inspection is performed with the inspection optical system.

According to such a configuration, a compact ophthalmologic apparatus that can objectively measure the subject's eye by the refractive power measurement optical system arranged in the transmission direction of the optical path separating unit and can inspect the subject's eye by the inspection optical system arranged in the reflection direction of the optical path separating unit can be provided.

In the ophthalmologic apparatus according to some embodiments, the optical path separating unit includes two or more wavelength separation elements (first filter 711, second filter 712) that have different wavelength separation characteristics each other and a movement mechanism (720) configured to selectively arrange the two or more wavelength separation elements in the optical path of the refractive power measurement optical system.

According to such a configuration, the optical axes before and after changing the wavelength separation characteristics can be matched, since the two or more wavelength separation elements are selectively arranged in the optical path of the refractive power measurement optical system. Thereby, highly accurate measurement and inspection by the refractive power measurement optical system and the inspection optical system can be performed.

In the ophthalmologic apparatus according to some embodiments, the inspection optical system includes a fixation optical system (fixation projection system 4) configured to project fixation light (400 nm to 700 nm) onto the subject's eye and an optical path coupling member (dichroic mirror 83) that combines an optical path of the fixation optical system with an optical path of the light in the second wavelength range. The wavelength separation characteristics are changed so as to guide the fixation light to the objective lens when a measurement is performed with the refractive power measurement optical system and when an inspection is performed with the inspection optical system.

According to such a configuration, the subject's eye can be objectively measured by the refractive power measurement optical system and the subject's eye can be inspected by the inspection optical system, in a state where the fixation light is projected onto the subject's eye while performing optimum wavelength separation by the optical path separating unit. Thereby, highly accurate measurement by the refractive power measurement optical system and highly accurate inspection by the inspection optical system can be performed.

In the ophthalmologic apparatus according to some embodiments, the inspection optical system includes an interference optical system configured to split the light (L0) in the second wavelength range from a light source (OCT light source 101) into reference light (LR) and measurement light (LS), to project the measurement light onto the subject's eye, and to detect interference light (LC) between returning light of the measurement light from the subject's eye and the reference light.

According to such a configuration, even in the case where at least part of the first wavelength range and the second wavelength range overlap, the optimum wavelength separation can be performed by the optical path separating unit. Thereby, the highly accurate measurement and inspection using the refractive power measurement optical system and the interference optical system can be performed. In addition, by sharing the objective lens, a compact ophthalmologic apparatus including the interference optical system on the basis of the configuration of the refractive power measurement optical system can be provided.

In the ophthalmologic apparatus according to some embodiments, the inspection optical system includes a subjective inspection optical system (visual target projection system) configured to project visual target light in the second wavelength range (400 nm to 700 nm) onto the subject's eye. The wavelength separation characteristics have characteristics of guiding the visual target light to the objective lens when the inspection is performed with the subjective optical system.

According to such a configuration, even in the case where at least part of the first wavelength range and the second wavelength range overlap, the optimum wavelength separation can be performed by the optical path separating unit. Thereby, the highly accurate measurement and inspection using the refractive power measurement optical system and the subjective inspection optical system can be performed. In addition, by sharing the objective lens, a compact ophthalmologic apparatus including the subjective inspection optical system on the basis of the configuration of the refractive power measurement optical system can be provided.

In the ophthalmologic apparatus according to some embodiments, at least a part of the inspection optical system is configured to be capable of replacing with an optical system included in any of two or more measurement units which are selectively attachable.

According to such a configuration, even in the case where at least part of the first wavelength range and the second wavelength range overlap, a compact ophthalmologic apparatus capable of performing an arbitrary inspection on the basis of the configuration of the refractive power measurement optical system can be provided.

In the ophthalmologic apparatus according to some embodiments, the two or more measurement units include a first measurement unit including an interference optical system configured to split the light (L0) in the second wavelength range from a light source (OCT light source 101) into reference light (LR) and measurement light (LS), to project the measurement light onto the subject's eye, and to detect interference light (LC) between returning light of the measurement light from the subject's eye and the reference light, and a second measurement unit including a subjective inspection optical system (visual target projection system) configured to visual target light in the second wavelength range (400 nm to 700 nm) onto the subject's eye.

According to such a configuration, even in the case where at least part of the first wavelength range and the second wavelength range overlap, a compact ophthalmologic apparatus including an optical system which is capable of selectively mounting the interference optical system and the subjective inspection optical system on the basis of the configuration of the refractive power measurement optical system can be provided.

<Others>

The above-described embodiments are merely examples for carrying out the present invention. Those who intend to implement the present invention can apply any modification, omission, addition, or the like within the scope of the gist of the present invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
   an objective lens;
   a refractive power measurement optical system configured to project light in a first wavelength range onto a subject's eye via the objective lens and to detect returning light from the subject's eye;
   an inspection optical system configured to project light in a second wavelength range onto the subject's eye via the objective lens; and
   an optical path separating unit that is arranged in an optical path of the refractive power measurement optical system and is configured to separate an optical path of the inspection optical system from the optical path of the refractive power measurement optical system by performing wavelength separation based on changeable wavelength separation characteristics, and
   the optical path separating unit is further configured to change at least one of a transmission wavelength characteristic of incident light and a reflection wavelength characteristic of the incident light.

2. The ophthalmologic apparatus of claim 1, wherein the wavelength separation characteristics are changed so as to perform wavelength separation for the light in the first wavelength range and the light in the second wavelength range according to a type of inspection.

3. The ophthalmologic apparatus of claim 2, wherein the refractive power measurement optical system is arranged in an optical path of light reflected by the optical path separating unit,
   the inspection optical system is arranged in an optical path of light transmitted through the optical path separating unit, and
   the wavelength separation characteristics are changed so that the light in the first wavelength range is reflected by the optical path separating unit and the light in the second wavelength range is transmitted through the optical path separating unit when a measurement is performed with the refractive power measurement optical system and are changed so that the light in the first wavelength range is transmitted through the optical path separating unit and the light in the second wavelength range is transmitted through the optical path separating unit when an inspection is performed with the inspection optical system.

4. The ophthalmologic apparatus of claim 2, wherein the refractive power measurement optical system is arranged in an optical path of light transmitted through the optical path separating unit,
   the inspection optical system is arranged in an optical path of light reflected by the optical path separating unit, and
   the wavelength separation characteristics are changed so that the light in the first wavelength range is transmitted through the optical path separating unit and the light in the second wavelength range is reflected by the optical path separating unit when a measurement is performed with the refractive power measurement optical system and are changed so that the light in the first wavelength range is reflected by the optical path separating unit and the light in the second wavelength range is reflected by the optical path separating unit when an inspection is performed with the inspection optical system.

5. The ophthalmologic apparatus of claim 1, wherein the optical path separating unit comprises:
   two or more wavelength separation elements that have different wavelength separation characteristics each other; and
   a movement mechanism configured to selectively arrange the two or more wavelength separation elements in the optical path of the refractive power measurement optical system.

6. The ophthalmologic apparatus of claim 1, wherein the inspection optical system comprises:
   a fixation optical system configured to project fixation light onto the subject's eye; and
   an optical path coupling member that combines an optical path of the fixation optical system with an optical path of the light in the second wavelength range, and
   the wavelength separation characteristics are changed so as to guide the fixation light to the objective lens when a measurement is performed with the refractive power measurement optical system and when an inspection is performed with the inspection optical system.

7. The ophthalmologic apparatus of claim 1, wherein the inspection optical system comprises an interference optical system configured to split the light in the second wavelength range from a light source into reference light and measurement light, to project the measurement light onto the subject's eye, and to detect interference light between returning light of the measurement light from the subject's eye and the reference light.

8. The ophthalmologic apparatus of claim 1, wherein the inspection optical system comprises a subjective inspection optical system configured to project visual target light in the second wavelength range onto the subject's eye, and the wavelength separation characteristics have characteristics of guiding the visual target light to the objective lens when the inspection is performed with the subjective optical system.

9. The ophthalmologic apparatus of claim 1, wherein at least a part of the inspection optical system is configured to be capable of replacing with an optical system included in any of two or more measurement units which are selectively attachable.

10. The ophthalmologic apparatus of claim 9, wherein the two or more measurement units comprise:

a first measurement unit including an interference optical system configured to split the light in the second wavelength range from a light source into reference light and measurement light, to project the measurement light onto the subject's eye, and to detect interference light between returning light of the measurement light from the subject's eye and the reference light; and a second measurement unit including a subjective inspection optical system configured to visual target light in the second wavelength range onto the subject's eye.

11. An ophthalmologic apparatus comprising:

an objective lens;

a refractive power measurement optical system including a first optical component and configured to project light in a first wavelength range onto a subject's eye via the objective lens and to detect returning light from the subject's eye;

an inspection optical system including a second optical component and configured to project light in a second wavelength range onto the subject's eye via the objective lens; and a filter that is arranged in an optical path of the refractive power measurement optical system and is configured to separate an optical path of the inspection optical system from the optical path of the refractive power measurement optical system by performing wavelength separation based on changeable wavelength separation characteristics, and the filter is further configured to change at least one of a transmission wavelength characteristic of incident light and a reflection wavelength characteristic of the incident light.

* * * * *